(12) United States Patent
Boldingh et al.

(10) Patent No.: US 7,220,885 B2
(45) Date of Patent: *May 22, 2007

(54) CATALYST TREATMENT USEFUL FOR AROMATICS CONVERSION PROCESS

(75) Inventors: Edwin P. Boldingh, Arlington Heights, IL (US); Antoine Negiz, Wilmette, IL (US); Gregory F. Maher, Aurora, IL (US); Paula L. Bogdan, Mount Prospect, IL (US); Dean E. Rende, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/855,463

(22) Filed: May 27, 2004

(65) Prior Publication Data

US 2005/0266979 A1   Dec. 1, 2005

(51) Int. Cl.
*C07C 5/22* (2006.01)
*C07C 2/64* (2006.01)
*B01J 21/00* (2006.01)
*B01J 29/00* (2006.01)
*B01J 29/18* (2006.01)

(52) U.S. Cl. .................. 585/475; 585/448; 502/74; 502/77; 502/78; 502/216; 502/238; 502/240; 502/256

(58) Field of Classification Search .............. 502/74, 502/77, 78, 216, 238, 240, 256; 585/448, 585/475

See application file for complete search history.

(56) References Cited

U.S. PATENT DOCUMENTS

| 3,702,886 A | 11/1972 | Argauer et al. ........... 423/328 |
| 3,709,979 A | 1/1973 | Chu ........................... 423/328 |
| 3,832,449 A | 8/1974 | Rosinski et al. ........... 423/328 |
| 3,849,340 A | 11/1974 | Pollitzer ................ 252/455 Z |
| RE28,341 E | 2/1975 | Wadlinger et al. ......... 208/120 |
| 4,076,842 A | 2/1978 | Plank et al. ............... 423/328 |
| 4,159,282 A | 6/1979 | Olson et al. ............... 585/481 |
| 4,163,018 A | 7/1979 | Tada et al. ............... 260/429.9 |
| 4,183,827 A * | 1/1980 | Adams et al. ............. 502/223 |
| 4,241,036 A | 12/1980 | Flanigen et al. ........... 423/328 |
| 4,278,565 A | 7/1981 | Chen et al. ............ 252/455 Z |
| 4,365,104 A | 12/1982 | Kaeding .................... 585/467 |
| 4,409,413 A * | 10/1983 | Iwayama et al. ........... 585/481 |
| 4,418,006 A * | 11/1983 | Kim et al. ..................... 502/73 |
| 4,440,871 A | 4/1984 | Lok et al. .................. 502/214 |
| 4,537,754 A | 8/1985 | Casci et al. ................ 423/277 |
| 4,556,477 A | 12/1985 | Dwyer ....................... 208/111 |

(Continued)

FOREIGN PATENT DOCUMENTS

EP  0 378 916 B1  11/1992

*Primary Examiner*—David Sample
*Assistant Examiner*—Patricia L. Hailey
(74) *Attorney, Agent, or Firm*—Maryann Maas

(57) ABSTRACT

A process for preparing a transalkylation catalyst, the catalyst itself, and a transalkylation process for using the catalyst are herein disclosed. The catalyst comprises rhenium metal on a solid-acid support such as mordenite, which has been treated with a sulfur-based agent. Such treatment reduces the amount of methane produced by metal hydrogenolysis in a transalkylation process wherein heavy aromatics like $A_9+$ are reacted with toluene to produce xylenes. Reduced methane production relative to total light ends gas production results in lower hydrogen consumption and lower reactor exotherms.

18 Claims, 2 Drawing Sheets

U.S. PATENT DOCUMENTS

| | | | |
|---|---|---|---|
| 4,567,029 A | 1/1986 | Wilson et al. | 423/306 |
| 4,857,666 A * | 8/1989 | Barger et al. | 585/323 |
| 5,004,855 A * | 4/1991 | Tada et al. | 585/489 |
| 5,296,208 A | 3/1994 | Lesch | 423/700 |
| 5,434,326 A * | 7/1995 | Gajda et al. | 585/467 |
| 5,672,796 A * | 9/1997 | Froment et al. | 585/419 |
| 5,723,710 A * | 3/1998 | Gajda et al. | 585/467 |
| 5,763,720 A | 6/1998 | Buchanan et al. | 585/475 |
| 5,905,051 A * | 5/1999 | Wu et al. | 502/60 |
| 6,060,417 A | 5/2000 | Kato et al. | 502/66 |
| 6,486,372 B1 * | 11/2002 | Merlen et al. | 585/467 |
| 6,613,709 B1 | 9/2003 | Merlen et al. | 502/64 |
| 6,815,570 B1 * | 11/2004 | Negiz et al. | 585/475 |
| 6,864,400 B2 * | 3/2005 | Merlen et al. | 585/475 |
| 2005/0202955 A1 | 9/2005 | McMinn et al. | 502/64 |

* cited by examiner

CATALYST TREATMENT USEFUL FOR AROMATICS CONVERSION PROCESS

FIELD OF THE INVENTION

This invention relates to catalytic hydrocarbon conversion, and more specifically to the use of a metal-stabilized solid-acid catalyst for transalkylation of heavy aromatics such as $C_9^+$ compounds with toluene to produce xylenes. By pretreating a rhenium containing zeolitic catalyst with sulfur, undesired methane formation is reduced.

BACKGROUND OF THE INVENTION

Xylene isomers, para-xylene, meta-xylene and ortho-xylene, are important intermediates which find wide and varied application in chemical syntheses. Para-xylene upon oxidation yields terephthalic acid, which is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates, and further comprise ethylbenzene, which is difficult to separate or to convert. Para-xylene in particular is a major chemical intermediate with rapidly growing demand, but amounts to only 20 to 25% of a typical $C_8$ aromatics stream. Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Often toluene ($C_7$) is dealkylated to produce benzene ($C_6$) or selectively disproportionated to yield benzene and $C_8$ aromatics from which the individual xylene isomers are recovered.

A current objective of many aromatics complexes is to increase the yield of xylenes and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. A higher yield of xylenes at the expense of benzene thus is a favorable objective, and processes to transalkylate $C_9$ and heavier aromatics with benzene and toluene have been commercialized to obtain high xylene yields.

U.S. Pat. No. 4,365,104 discloses a process for modifying ZSM-5 type zeolite catalysts with sulfur-based treating agents in order to enhance para-selective catalyst properties based upon the molecular sieve.

U.S. Pat. No. 4,857,666 discloses a transalkylation process over mordenite and suggests modifying the mordenite by steam deactivation or incorporating a metal modifier into the catalyst.

U.S. Pat. No. 5,763,720 discloses a transalkylation process for conversion of $C_9^+$ into mixed xylenes and $C_{10}^+$ aromatics over a catalyst containing zeolites illustrated in a list including amorphous silica-alumina, MCM-22, ZSM-12, and zeolite beta, where the catalyst further contains a Group VIII metal such as platinum. Treatment to reduce aromatics loss by ring hydrogenation over such a catalyst includes sulfur exposure.

U.S. Pat. No. 6,060,417 discloses a transalkylation process using a catalyst based on mordenite with a particular zeolitic particle diameter and having a feed stream limited to a specific amount of ethyl containing heavy aromatics. Said catalyst contains nickel or rhenium metal.

U.S. Pat. No. 6,486,372 discloses a transalkylation process using a catalyst based on dealuminated mordenite with a high silica to alumina ratio that also contains at least one metal component.

U.S. Pat. No. 6,613,709 discloses a catalyst for transalkylation comprising zeolite structure type NES and metals such as rhenium, indium, or tin. The use of sulfur is disclosed, but Example 4 shows a sulfurization step (called sulphurization) that is only performed on a catalyst $C_2$ containing nickel, which is described as 'not in Accordance with the Invention'. Also, nothing is disclosed about the effect of sulfur on methane yield.

Many types of supports and elements have been disclosed for use as catalysts in processes to transalkylate various types of aromatics into xylenes, but the problem presented by high methane production associated with rhenium containing catalysts appears to have gone as yet unrecognized in the art. Applicants have found a solution with specific sulfur treatment of rhenium supported on solid-acid catalysts that increases yield of xylenes and decreases yield of undesired methane, which is associated with high metal hydrogenolysis activity. Avoidance of high metal hydrogenolysis activity becomes especially important under conditions of low total hydrogen partial pressure.

SUMMARY OF THE INVENTION

A principal object of the present invention is to provide a process for preparing a catalyst, the catalyst itself, and a process for the transalkylation of alkylaromatic hydrocarbons into xylenes. More specifically, the present invention is directed to converting aromatic hydrocarbons with decreased yields of methane. This invention is based on the discovery that a sulfided catalyst based on a solid-acid material in conjunction with a rhenium metal component exhibits decreased methane production when contacted under transalkylation conditions.

Accordingly, a broad embodiment of the present invention is a process for preparing a catalyst having a sulfur component, a rhenium component, and a solid-acid component. In another embodiment, the present invention is a transalkylation process for using the catalyst to convert aromatics into xylenes with decreased methane production. In yet another embodiment, the present invention is the catalyst itself having a solid-acid component such as mordenite, mazzite, zeolite beta, ZSM-11, ZSM-12, ZSM-22, ZSM-23, MFI topology zeolite, NES topology zeolite, EU-1, MAPO-36, MAPSO-31, SAPO-5, SAPO-11, SAPO-41, and silica-alumina. The catalyst also has an essential rhenium metal component and a sulfur component.

These, as well as other objects and embodiments will become evident from the following detailed description of the invention.

DETAILED DESCRIPTION OF THE INVENTION

Figure 1:
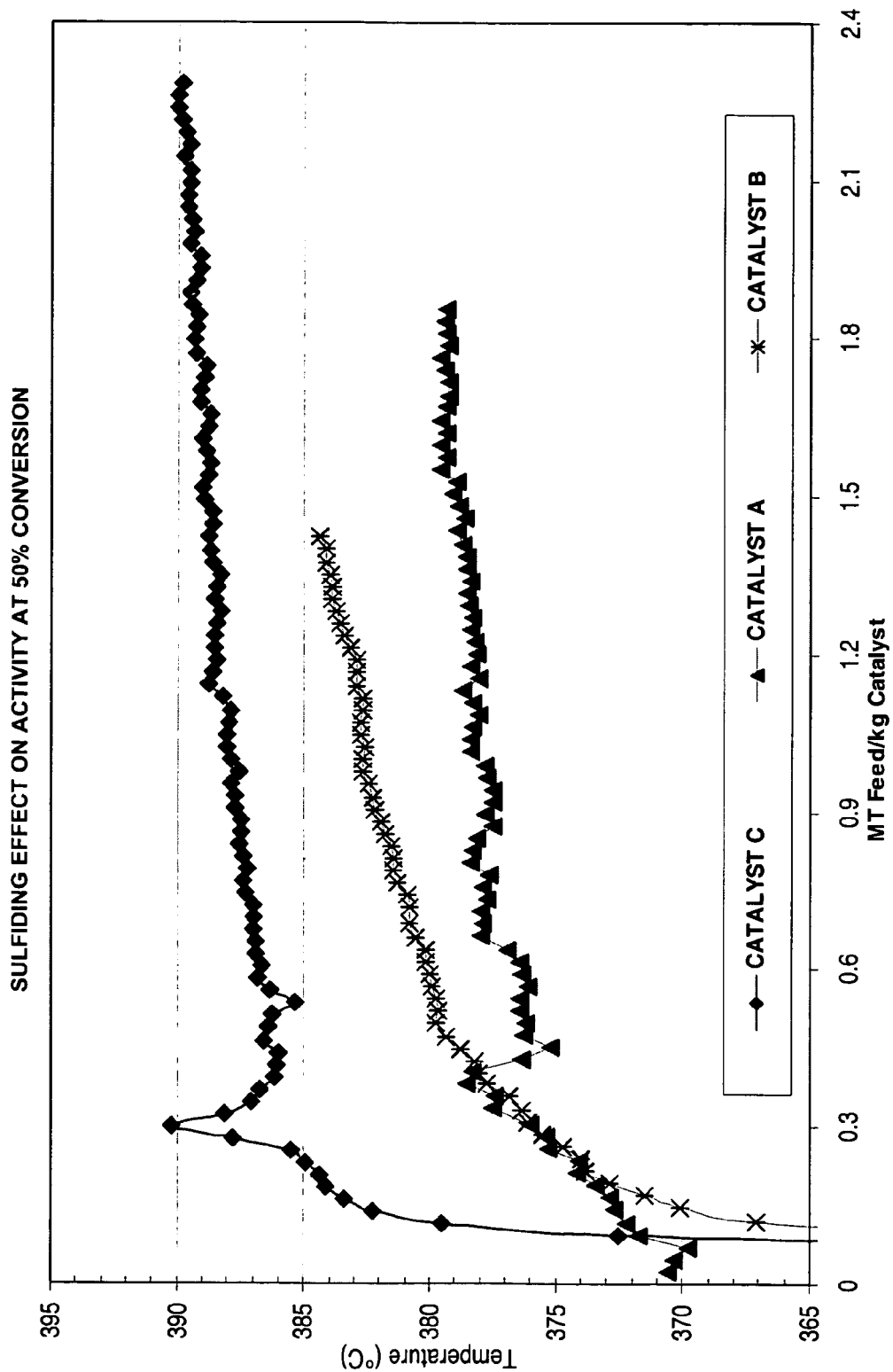
FIG. 1 shows the effect of sulfiding rhenium catalyst on activity for the transalkylation of $C_7$, $C_9$, and $C_{10}$ aromatics at a level of about 50 wt-% conversion while producing $C_8$ aromatics.

The feed stream to the present process generally comprises alkylaromatic hydrocarbons of the general formula $C_6H_{(6-n)}R_n$, where n is an integer from 0 to 6 and R is $CH_3$, $C_2H_5$, $C_3H_7$, or $C_4H_9$, in any combination. Suitable alkylaromatic hydrocarbons include, for example but without so limiting the invention, benzene, toluene, ethylbenzene, ethyltoluenes, propylbenzenes, tetramethylbenzenes, ethyldimethylbenzenes, diethylbenzenes, methylpropylbenzenes, ethylpropylbenzenes, triethylbenzenes, di-isopropylbenzenes, and mixtures thereof. The feed stream may comprise lower levels of ortho-xylene, meta-xylene, and para-xylene that are the desired products of the present process.

The feed stream also may comprise naphthalene and other $C_{10}$ and $C_{11}$ aromatics and suitably is derived from one or a variety of sources. Polycyclic aromatics such as the bi-cyclic components including naphthalene, methylnaphthalene, are permitted in the feed stream of the present invention. Indane, which is also referred to as indan or indene, is meant to define a carbon number nine aromatic species with one carbon six ring and one carbon five ring wherein two carbon atoms are shared. Naphthalene is meant to define a carbon number ten aromatic species with two carbon six rings wherein two carbon atoms are shared. Polycyclic aromatics may also be present in amounts above the trace amounts permitted in prior art, and these amounts are herein defined as substantial amounts such as greater than about 0.5 wt-% of the feed stream.

Feed components may be produced synthetically, for example, from naphtha by catalytic reforming or by pyrolysis followed by hydrotreating to yield an aromatics-rich product. The feed stream may be derived from such product with suitable purity by extraction of aromatic hydrocarbons from a mixture of aromatic and nonaromatic hydrocarbons and fractionation of the extract. For instance, aromatics may be recovered from reformate. Reformate may be produced by any of the processes known in the art. The aromatics then may be recovered from reformate with the use of a selective solvent, such as one of the sulfolane type, in a liquid-liquid extraction zone. The recovered aromatics may then be separated into streams having the desired carbon number range by fractionation. When the severity of reforming or pyrolysis is sufficiently high, extraction may be unnecessary and fractionation may be sufficient to prepare the feed stream. Such fractionation typically includes at least one separation column to control feed end point.

The feed heavy-aromatics stream, characterized by $C_9^+$ aromatics (or $A_9^+$), permits effective transalkylation of light aromatics such as benzene and toluene with the heavier $C_9^+$ aromatics to yield additional $C_8$ aromatics that are preferably xylenes. The heavy-aromatics stream preferably comprises at least about 90 wt-% total aromatics; and may be derived from the same or different known refinery and petrochemical processes as the benzene and toluene, and/or may be recycled from the separation of the product from transalkylation.

The feed stream is preferably transalkylated in the vapor phase and in the presence of hydrogen. If transalkylated in the liquid phase, then the presence of hydrogen is optional. If present, free hydrogen is associated with the feed stream and recycled hydrocarbons in an amount of from about 0.1 moles per mole of alkylaromatics up to 10 moles per mole of alkylaromatic. This ratio of hydrogen to alkylaromatic is also referred to as hydrogen to hydrocarbon ratio. The transalkylation reaction preferably yields a product having an increased xylene content. High yields of methane are undesired as they generally accompany high consumption of hydrogen, high exotherms across a reactor, and may decrease total yields of xylenes. High metal hydrogenolysis activity present in a rhenium containing catalyst causes a shift of light ends gases to even lighter gas species, specifically causing methane to increase at the expense of ethane, propane, butane, and pentane. Such a methane increase consumes hydrogen and increases reactor exotherms, both of which lead to economic problems associated with increased utilities for heat and for hydrogen supply. Also, xylenes increase when total hydrogen partial pressure is reduced relative to higher levels of hydrogen; such relatively lower levels of total hydrogen, if any is present at all, favor reduced loss of aromatic rings by hydrogen saturation.

The feed to a transalkylation reaction zone usually first is heated by indirect heat exchange against the effluent of the reaction zone and then is heated to reaction temperature by exchange with a warmer stream, steam or a furnace. The feed then is passed through a reaction zone, which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of an effluent stream comprising unconverted feed and product hydrocarbons. This effluent is normally cooled by indirect heat exchange against the stream entering the reaction zone and then further cooled through the use of air or cooling water. The effluent may be passed into a stripping column in which substantially all $C_5$ and lighter hydrocarbons present in the effluent are concentrated into an overhead stream and removed from the process. An aromatics-rich stream is recovered as net stripper bottoms which is referred to herein as the transalkylation effluent.

To effect a transalkylation reaction, the present invention incorporates a transalkylation catalyst in at least one zone, but no limitation is intended in regard to a specific catalyst other than such catalyst must possess a solid-acid component and a rhenium metal component. Conditions employed in the transalkylation zone normally include a temperature of from about 200° to about 540° C. The transalkylation zone is operated at moderately elevated pressures broadly ranging from about 100 kPa to about 6 MPa absolute. The transalkylation reaction can be effected over a wide range of space velocities. Weight hourly space velocity (WHSV) generally is in the range of from about 0.1 to about 20 $hr^{-1}$.

The transalkylation effluent is separated into a light recycle stream, a mixed $C_8$ aromatics product and a heavy recycle stream. The mixed $C_8$ aromatics product can be sent for recovery of para-xylene and other valuable isomers. The light recycle stream may be diverted to other uses such as to benzene and toluene recovery, but alternatively is recycled partially to the transalkylation zone. The heavy recycle stream contains substantially all of the $C_9$ and heavier aromatics and may be partially or totally recycled to the transalkylation reaction zone.

Several types of transalkylation catalysts that may be used in the present invention are based on a solid-acid material combined with a metal component. Suitable solid-acid materials include all forms and types of mordenite, mazzite (omega zeolite), beta zeolite, ZSM-11, ZSM-12, ZSM-22, ZSM-23, MFI type zeolite, NES type zeolite, EU-1, MAPO-36, MAPSO-31, SAPO-5, SAPO-11, SAPO-41, silica-alumina mixtures thereof or ion exchanged versions of such solid-acids. For example, in U.S. Pat. No. 3,849,340 a catalytic composite is described comprising a mordenite component having a $SiO_2/Al_2O_3$ mole ratio of at least 40:1 prepared by acid extracting $Al_2O_3$ from mordenite prepared with an initial $SiO_2/Al_2O_3$ mole ratio of less than 30:1 and a metal component selected from copper, silver and zirconium. Refractory inorganic oxides, combined with the above-mentioned and other known catalytic materials, have been found useful in transalkylation operations. For instance, silica-alumina is described in U.S. Pat No. 5,763,720. Crystalline aluminosilicates have also been employed in the art as transalkytation catalysts. ZSM-12 is more particularly described in U.S. Pat. No. 3,832,449. Zeolite beta is more particularly described in Re. 28,341 (of original U.S. Pat. No. 3,308,069). A favored form of zeolite beta is described in U.S. Pat. No. 5,723,710, which is incorporated herein by reference. The preparation of MFI topology zeolite is also well known in the art. in one method, the zeolite is prepared by crystallizing a mixture containing an alumina source, a silica source, an alkali metal source, water and an alkyl ammonium compound or its precursor. Further descriptions are in U.S. Pat. No. 4,159,282, U.S. Pat. No. 4,163,018, and U.S. Pat. No. 4,278,565.

Other suitable solid-acid materials include mazzite, ZSM-11, ZSM-22, ZSM-23, NES type zeolite, EU-1, MAPO-36, MAPSO-31, SAPO-5, SAPO-11, SAPO-41. Preferred mazzite zeolites include Zeolite Omega. The synthesis of the Zeolite Omega is described in U.S. Pat. No. 4,241,036. ZSM intermediate pore size zeolites useful in this invention include ZSM-5 (U.S. Pat. No. 3,702,886); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842). European Patent EP 0378916 B1 describes NES type zeolite and a method for preparing NU-87. The EUO structural-type EU-1 zeolite is described in U.S. Pat. No. 4,537,754. MAPO-36 is described in U.S. Pat. No. 4,567,029. MAPSO-31 is described in U.S. Pat. No. 5,296,208 and typical SAPO compositions are described in U.S. Pat. No. 4,440,871 including SAPO-5, SAPO-11 and SAPO-41.

A refractory binder or matrix is optionally utilized to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphate, zinc oxide and silica. Alumina is a preferred binder.

The catalyst also contains an essential rhenium metal component. This component may exist within the final catalytic composite as a compound such as an oxide, sulfide, halide, or oxyhalide, in chemical combination with one or more of the other ingredients of the composite. The rhenium metal component may be incorporated in the catalyst in any suitable manner, such as coprecipitation, ion-exchange, co-mulling or impregnation. The preferred method of preparing the catalyst involves the utilization of a soluble, decomposable compound of rhenium metal to impregnate the carrier material in a relatively uniform manner. Typical rhenium compounds which may be employed include ammonium perrhenate, sodium perrhenate, potassium perrhenate, potassium rhenium oxychloride, potassium hexachlororhenate (IV), rhenium chloride, rhenium heptoxide, perrhenic acid, and the like compounds. Preferably, the compound is ammonium perrhenate or perrhenic acid because no extra steps may be needed to remove any co-contaminant species. This component may be present in the final catalyst composite in any amount which is catalytically effective, generally comprising about 0.01 to about 2 wt-% of the final catalyst calculated on an elemental basis.

The catalyst may optionally contain additional modifier metal components. Preferred metal modifier components of the catalyst include, for example, tin, germanium, lead, indium, platinum, palladium and mixtures thereof. Catalytically effective amounts of such metal modifiers may be incorporated into the catalyst by any means known in the art. A preferred amount is a range of about 0.01 to about 2.0 wt-% on an elemental basis.

One shape of the catalyst of the present invention is a cylinder. Such cylinders can be formed using extrusion methods known to the art. Another shape of the catalyst is one having a trilobal or three-leaf clover type of cross section that can be formed by extrusion. Another shape is a sphere that can be formed using oil-dropping methods or other forming methods known to the art.

At least one oxidation step may be used in the preparation of the catalyst. The conditions employed to effect the oxidation step are selected to convert substantially all of the metallic components within the catalytic composite to their corresponding oxide form. The oxidation step typically takes place at a temperature of from about 370° to about 650° C. An oxygen atmosphere is employed typically comprising air. Generally, the oxidation step will be carried out for a period of from about 0.5 to about 10 hours or more, the exact period of time being that required to convert substantially all of the metallic components to their corresponding oxide form. This time will, of course, vary with the oxidation temperature employed and the oxygen content of the atmosphere employed.

In preparing the catalyst, a reduction step may optionally be employed. The reduction step is designed to reduce substantially all of the metal components to the corresponding elemental metallic state and to ensure a relatively uniform and finely divided dispersion of this component throughout the catalyst. It is preferred that the reduction step take place in a substantially water-free environment. Preferably, the reducing gas is substantially pure, dry hydrogen (i.e., less than 20 wt-ppm water). However, other gases may be present such as CO, nitrogen, etc. Typically, the reducing gas is contacted with the oxidized catalytic composite at conditions including a reduction temperature of from about 315° to about 650° C. for a period of time of from about 0.5 to 10 or more hours effective to reduce at least about 80 wt-%, or more preferably substantially all of the rhenium metal component to the elemental metallic state. The preferred reduction conditions include a temperature of greater than about 400° C. for a time of greater than about 2.5 hours. The reduction step may be performed under atmospheric pressure or at higher pressures. The reduction step may be performed prior to loading the catalytic composite into the hydrocarbon conversion zone or it may be performed in situ as part of a hydrocarbon conversion process start-up procedure. However, if this latter technique is employed, proper precautions must be taken to pre-dry the conversion unit to a substantially water-free state, and a substantially water-free reducing gas should be employed.

Finally, the catalytic composite is subjected to an essential sulfur treatment or pre-sulfiding step. The sulfur component may be incorporated into the catalyst by any known technique. Any one or a combination of in situ and/or ex situ sulfur treatment methods is preferred. The resulting catalyst mole ratio of sulfur to rhenium is preferably from about 0.1 to less than about 1.5, and even more preferably the catalyst mole ratio of sulfur to rhenium is about 0.3 to about 0.8.

A catalyst pretreatment ex situ is one method for minimizing the methane production of the catalyst composition by exposing it to sulfur. Effective treatment is accomplished by contacting the catalyst with a source of sulfur at a temperature ranging from about 0° to about 500° C., with room temperature providing satisfactory results. The source of sulfur can be contacted with the catalyst directly or via a carrier gas, typically, an inert gas such as hydrogen or nitrogen. In this embodiment, the source of sulfur is typically hydrogen sulfide.

The catalyst composition can also be treated in situ where a source of sulfur is contacted with the catalyst composition by adding it to the hydrocarbon feed stream in a concentration ranging from about 1 ppmw sulfur to about 10,000 ppmw sulfur. The need to add a sulfur source to the hydrocarbon feed stream may be reduced or eliminated entirely depending on the actual content of sulfur which may already be present in some hydrocarbon streams. Any sulfur compound that will decompose to form $H_2S$ and, optionally, a light hydrocarbon at about 500° C. or less will suffice. Typical examples of appropriate sources of sulfur include carbon disulfide and alkylsulfides such as methylsulfide, dimethylsulfide, dimethyldisulfide, diethylsulfide and dibutylsulfide. Typically, sulfur treatment is initiated by incorporating a source of sulfur into the feed and continuing sulfur treatment for a few days, typically, up to 10 days, more specifically, from one to five days. The sulfur treatment may be monitored by measuring the concentration of sulfur in the product off gas. The time calculated for sulfur treatment will depend on the actual concentration of sulfur in the feed and the desired sulfur loading to be achieved on the catalyst.

The catalyst can be contacted with sulfur during service by co-feeding sulfur to the reactor in varied amounts via the hydrogen stream entering the reactor or the hydrocarbon feedstock. The sulfur can be continuously added to the feedstock throughout the process cycle or the sulfur can be intermittently continuously added in which this sulfur is co-fed continuously for a period of time, discontinued, then co-fed again.

EXAMPLES

The following examples are presented only to illustrate certain specific embodiments of the invention, and should not be construed to limit the scope of the invention as set forth in the claims. There are many possible other variations, as those of ordinary skill in the art will recognize, within the scope of the invention.

Example 1

Samples of catalysts comprising mordenite were prepared for comparative pilot-plant testing by the forming process called extrusion. Typically, 2500 g of a powder blend of 25 wt-% alumina (commercially available under the trade names Catapal™ B and/or Versal™ 250) and 75 wt-% mordenite (commercially available under the trade name Zeolyst™ CBV-21A) was added to a mixer. A solution was prepared using 10 g nitric acid (67.5 wt-% $HNO_3$) with 220 g deionized water and the solution was stirred. The solution was added to the powder blend in the mixer, and mulled to make dough suitable for extrusion. The dough was extruded through a die plate to form cylindrically shaped (0.16 cm diameter) extrudate particles. The extrudate particles were calcined at about 565° C. with 15 wt-% steam for 2 hours.

Four different catalysts were finished using the extrudate particles and an evaporative impregnation with rhenium metal by using an aqueous solution of ammonium perrhenate ($NH_4ReO_4$). The impregnated base was calcined in air at 540° C. for 2 hours and resulted in a metal level of 0.4 wt-% rhenium. Next the catalysts were reduced for 12 hours in hydrogen at 500° C. Then the catalysts were sulfided using an injection of hydrogen sulfide ($H_2S$) gas into a mixed sample in a rotating vessel for even sulfur distribution over the catalyst particles. Catalyst A was finished at a molar ratio of sulfur to rhenium of 0.5 mol S/mol Re. Catalyst B was finished at a molar ratio of sulfur to rhenium of 0.8 mol S/mol Re. Catalyst D did not undergo sulfiding and thus represented a catalyst of the prior art. Catalyst C did not undergo either sulfiding or the final reduction step for 12 hours; instead it only was reduced in hydrogen for approximately 3 hours.

Example 2

Figure 2:
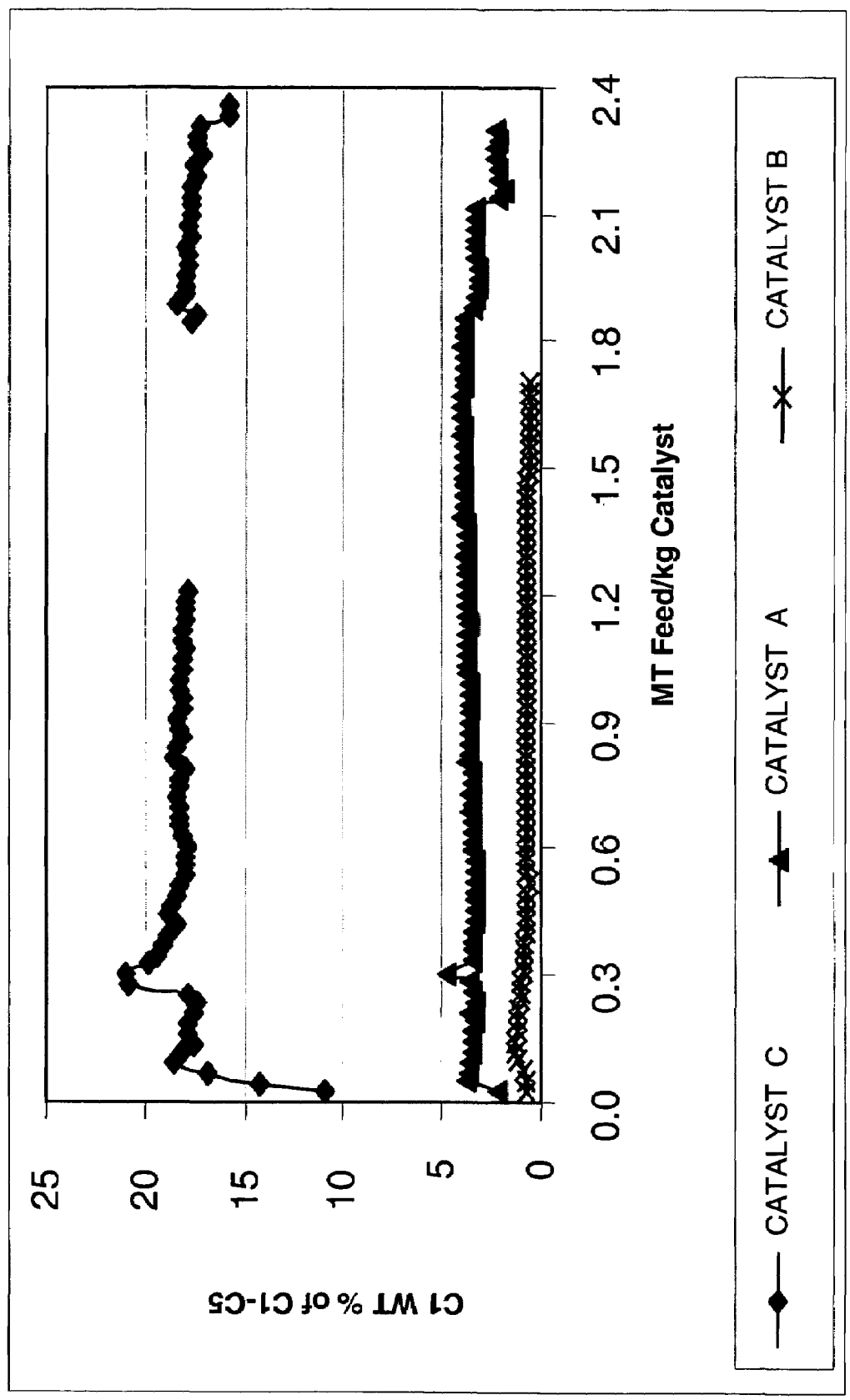
FIG. 2 shows the effect of sulfiding rhenium catalyst on methane ($C_1$) selectivity, shown as wt-% of total $C_1$ to $C_5$ produced by the process.

Catalysts A, B, C, and D were tested for aromatics transalkylation ability in a pilot plant using an aromatics feed blend of $C_7$, $C_9$, and $C_{10}$ aromatics to demonstrate effectiveness of catalyst presulfiding in controlling methane production when producing $C_8$ aromatics. The test consisted of loading a vertical reactor with catalyst and contacting the feed at 2860 kPa abs (400 psig) under a space velocity (WHSV) of 2 $hr^{-1}$ and hydrogen to hydrocarbon ratio ($H_2$/HC) of 4. A conversion level of about 50 wt-% of feed aromatics was achieved. FIG. 1 shows the results on catalyst activity as measured by a weighted average bed temperature, and FIG. 2 shows the results on catalyst methane production as a weighted percentage of light ends that includes $C_1$ through $C_5$ compounds.

The data showed that sulfiding of a rhenium containing catalyst served to reduce the methane production during an aromatics transalkylation reaction. Accordingly, the reduced methane production is understood to be accompanied by less hydrogen consumption and a lower exotherm associated with reduced metal hydrogenolysis of lighter carbon number material, and correspondingly improved yields of desired xylene species from the transalkylation process when operated at lower total hydrogen partial pressures.

What is claimed is:

1. A process for preparing a transalkylation catalyst comprising contacting the catalyst comprising a rhenium component, a solid-acid component, and an optional binder, with a sulfur-based treating agent effective for decreasing yields of methane under transalkylation conditions to form a catalyst consisting essentially of a rhenium component, a solid-acid component, an optional binder, and a sulfur component wherein the catalyst mole ratio of sulfur to rhenium is about 0.3 to about 0.8 and wherein the solid-acid component is selected from the group consisting of:

(A) mordenite having a $SiO_2/Al_2O_3$ ratio from about 20 to about 40, mazzite, zeolite beta, ZSM-12, ZSM-22, ZSM-23, EU-1, MAPO-36, MAPSO-31, SAPO-5, SAPO-11, SAPO-41, silica-alumina, mixtures thereof, (B) ZSM-11 in combination with at least one of mordenite having a $SiO_2/Al_2O_3$ ratio from about 20 to about 40, mazzite, zeolite beta, ZSM-12, ZSM-22, ZSM-23, EU-1, MAPO-36, MAPSO-31, SAPO-5, SAPO-11, SAPO-41, or silica-alumina and (C) MFI topology zeolite in combination with at least one of mordenite having a $SiO_2/Al_2O_3$ ratio from about 20 to about 40, mazzite, zeolite beta, ZSM-12, ZSM-22, ZSM-23, EU-1, MAPO-36, MAPSO-31, SAPO-5, SAPO-11, SAPO-41, or silica-alumina.

2. The process of claim 1 wherein the sulfur-based treating agent is selected from the group consisting of carbon disulfide, methylsulfide, dimethylsulfide, dimethyldisulfide, methylethylsulfide, diethylsulfide, dibutylsulfide, and mixtures thereof.

3. The process of claim 1 wherein the sulfur-based treating agent is hydrogen sulfide.

4. The process of claim 1 wherein the sulfur-based treating agent is provided in a treating medium comprising from about 25 to about 100 wt-% of the treating agent.

5. The process of claim 1 wherein the sulfur-based treating agent is provided in a hydrocarbon feed stream medium at a level above about 1 wt-ppm sulfur.

6. The process of claim 1 further comprising the step of reducing the catalyst at a temperature greater than about 400° C. in the presence of hydrogen for a time period greater than about 2.5 hours.

7. The process of claim 1 wherein the solid-acid component is selected from the group consisting of
   (A) mordenite having a $SiO_2/Al_2O_3$ ratio from about 20 to about 40, mazzite, zeolite beta, ZSM-12, ZSM-22, ZSM-23, EU-1, silica-alumina, mixtures thereof, and
   (B) ZSM-11 in combination with at least one of mordenite having a $SiO_2/Al_2O_3$ ratio from about 20 to about 40, mazzite, zeolite beta, ZSM-12, ZSM-22, ZSM-23, EU-1, or silica-alumina, and
   (C) MFI topology zeolite in combination with at least one of mordenite having a $SiO_2/Al_2O_3$ ratio from about 20 to about 40, mazzite, zeolite beta, ZSM-12, ZSM-22, ZSM-23, EU-1, or silica-alumina.

8. The process of claim 7 wherein the solid-acid component is mordenite having a $SiO_2/Al_2O_3$ ratio from about 20to about 40.

9. A process for converting a hydrocarbon feed comprising $C_9^+$ aromatic compounds and toluene compounds, the process comprising the step of contacting the feed with a transalkylation catalyst under transalkylation conditions, wherein the transalkylation catalyst consists essentially of a rhenium component, a solid-acid component, an optional binder, and a sulfur component wherein the catalyst mole ratio of sulfur to rhenium is about 0.3 to about 0.8 and wherein the solid-acid component is selected from the group consisting of
   (A) mordenite having a $SiO_2/Al_2O_3$ ratio from about 20 to about 40, mazzite, zeolite beta, ZSM-12, ZSM-22, ZSM-23, EU-1, MAPO-36, MAPSO-31, SAPO-5, SAPO-11, SAPO-41, silica-alumina, mixtures thereof,
   (B) ZSM-11 in combination with at least one of mordenite having a $SiO_2/Al_2O_3$ ratio from about 20 to about 40, mazzite, zeolite beta, ZSM-12, ZSM-22, ZSM-23, EU-1, MAPO-36, MAPSO-31, SAPO-5, SAPO-11, SAPO-41, or silica-alumina and
   (C) MFI topology zeolite in combination with at least one of mordenite having a $SiO_2/Al_2O_3$ ratio from about 20 to about 40, mazzite, zeolite beta, ZSM-12, ZSM-22, ZSM-23, EU-1, MAPO-36, MAPSO-31, SAPO-5, SAPO-11, SAPO-41, or silica-alumina.

10. The process of claim 9 further comprising the step of recovering a product comprising xylenes.

11. The process of claim 9 wherein the solid-acid component is selected from the group consisting of
   (A) mordenite having a $SiO_2/Al_2O_3$ ratio from about 20 to about 40, mazzite, zeolite beta, ZSM-12, ZSM-22, ZSM-23, EU-1, silica-alumina, mixtures thereof,
   (B) ZSM-11 in combination with at least one of mordenite having a $SiO_2/Al_2O_3$ ratio from about 20 to about 40, mazzite, zeolite beta, ZSM-12, ZSM-22, ZSM-23, EU-1, or silica-alumina, and
   (C) MFI topology zeolite in combination with at least one of mordenite having a $SiO_2/Al_2O_3$ ratio from about 20 to about 40, mazzite, zeolite beta, ZSM-12, ZSM-22, ZSM-23, EU-1, or silica-alumina.

12. The process of claim 11 wherein the solid-acid component is mordenite having a $SiO_2/Al_2O_3$ ratio from about 20 to about 40.

13. The process of claim 9 wherein the transalkylation conditions comprise a temperature from about 200° to about 540° C., a pressure from about 100 kPa to about 6 MPa absolute, and a space velocity from about 0.1 to about 20 $hr^{-1}$.

14. A catalyst for transalkylation of aromatics consisting essentially of a rhenium component, a solid-acid component, an optional binder, and a sulfur component wherein the catalyst mole ratio of sulfur to rhenium is about 0.3 to about 0.8 and wherein the solid-acid component is selected from the group consisting of:
   (A) mordenite having a $SiO_2/Al_2O_3$ ratio from about 20 to about 40, mazzite, zeolite beta, ZSM-12, ZSM-22, ZSM-23, EU-1, MAPO-36, MAPSO-31, SAPO-5, SAPO-11, SAPO-41, silica-alumina, mixtures thereof,
   (B) ZSM-11 in combination with at least one of mordenite having a $SiO_2/Al_2O_3$ ratio from about 20 to about 40, mazzite, zeolite beta, ZSM-12, ZSM-22, ZSM-23, EU-1, MAPO-36, MAPSO-31, SAPO-5, SAPO-11, SAPO-41, or silica-alumina and
   (C) MFI topology zeolite in combination with at least one of mordenite having a $SiO_2/Al_2O_3$ ratio from about 20 to about 40, mazzite, zeolite beta, ZSM-12, ZSM-22, ZSM-23, EU-1, MAPO-36, MAPSO-31, SAPO-5, SAPO-11, SAPO-41, or silica-alumina.

15. The catalyst of claim 14 wherein the solid-acid component is selected from the group consisting of
   (A) mordenite having a $SiO_2/Al_2O_3$ ratio from about 20 to about 40, mazzite, zeolite beta, ZSM-12, ZSM-22, ZSM-23, EU-1, silica-alumina, mixtures thereof,
   (B) ZSM-11 in combination with at least one of mordenite having a $SiO_2/Al_2O_3$ ratio from about 20 to about 40, mazzite, zeolite beta, ZSM-12, ZSM-22, ZSM-23, EU-1, or silica-alumina, and
   (C) MFI topology zeolite in combination with at least one of mordenite having a $SiO_2/Al_2O_3$ ratio from about 20 to about 40, mazzite, zeolite beta, ZSM-12, ZSM-22, ZSM-23, EU-1, or silica-alumina.

16. The catalyst of claim 15 wherein the solid-acid component is selected from the group consisting of mordenite having a $SiO_2/Al_2O_3$ ratio from about 20 to about 40, zeolite beta, silica-alumina, mixtures thereof, and at least one of mordenite having a $SiO_2/Al_2O_3$ ratio from about 20 to about 40, mazzite, zeolite beta, or silica-alumina in combination with MFI topology zeolite.

17. The catalyst of claim 16 wherein the solid-acid component is mordenite having a $SiO_2/Al_2O_3$ ratio from about 20 to about 40.

18. The catalyst of claim 14 wherein the binder is an inorganic oxide component.

* * * * *